United States Patent
Mash et al.

(10) Patent No.: US 9,394,294 B2
(45) Date of Patent: Jul. 19, 2016

(54) METHODS AND COMPOSITIONS FOR PREPARING AND PURIFYING NORIBOGAINE

(71) Applicant: DemeRx, Inc., Fort Lauderdale, FL (US)

(72) Inventors: Deborah C. Mash, Miami, FL (US); Richard D. Gless, Jr., Miami, FL (US)

(73) Assignee: DEMERX, INC., Fort Lauderdale, FL (US)

( * ) Notice: Subject to any disclaimer, the term of this patent is extended or adjusted under 35 U.S.C. 154(b) by 0 days.

(21) Appl. No.: 14/298,534

(22) Filed: Jun. 6, 2014

(65) Prior Publication Data

US 2014/0357741 A1    Dec. 4, 2014

Related U.S. Application Data

(63) Continuation-in-part of application No. 13/104,406, filed on May 10, 2011, now Pat. No. 8,765,737.

(60) Provisional application No. 61/333,476, filed on May 11, 2010, provisional application No. 61/419,772, filed on Dec. 3, 2010.

(51) Int. Cl.
| | |
|---|---|
| *B01J 41/20* | (2006.01) |
| *A61K 31/55* | (2006.01) |
| *C07D 453/00* | (2006.01) |
| *C07D 471/22* | (2006.01) |
| *B01D 15/36* | (2006.01) |
| *B01D 15/38* | (2006.01) |

(52) U.S. Cl.
CPC ............ *C07D 453/00* (2013.01); *B01D 15/363* (2013.01); *B01J 41/20* (2013.01); *C07D 471/22* (2013.01); *B01D 15/3833* (2013.01)

(58) Field of Classification Search
USPC .................................. 521/214.02, 30; 540/579
See application file for complete search history.

(56) References Cited

U.S. PATENT DOCUMENTS

| | | | |
|---|---|---|---|
| 2,813,873 A | 11/1957 | Janot, et al. |
| 2,877,229 A | 3/1959 | Taylor |
| 3,516,989 A | 6/1970 | Sallay |
| 3,557,126 A | 1/1971 | Sallay |
| 3,574,220 A | 4/1971 | Sallay |
| 3,639,408 A | 2/1972 | Nagata et al. |
| 3,715,361 A | 2/1973 | Epstein et al. |
| 3,716,528 A | 2/1973 | Nagata et al. |
| 3,875,011 A | 4/1975 | Rubenstein et al. |
| 4,107,288 A | 8/1978 | Oppenheim et al. |
| 4,272,541 A | 6/1981 | Kotick et al. |
| 4,375,414 A | 3/1983 | Strahilevitz |
| 4,422,955 A | 12/1983 | Bryant |
| 4,444,758 A | 4/1984 | Scherschlicht et al. |
| 4,462,941 A | 7/1984 | Lee et al. |
| 4,464,378 A | 8/1984 | Hussain |
| 4,499,096 A | 2/1985 | Lotsof |
| 4,573,995 A | 3/1986 | Chen et al. |
| 4,587,243 A | 5/1986 | Lotsof |
| 4,604,365 A | 8/1986 | O'Neill et al. |
| 4,620,977 A | 11/1986 | Strahilevitz |
| 4,626,539 A | 12/1986 | Aungst et al. |
| 4,661,492 A | 4/1987 | Lewis et al. |
| 4,668,232 A | 5/1987 | Cordes et al. |
| 4,737,586 A | 4/1988 | Potier et al. |
| 4,806,341 A | 2/1989 | Chien et al. |
| 4,857,523 A | 8/1989 | Lotsof |
| 5,026,697 A | 6/1991 | Lotsof |
| 5,075,341 A | 12/1991 | Mendelson et al. |
| 5,145,684 A | 9/1992 | Liversidge et al. |
| 5,149,538 A | 9/1992 | Granger et al. |
| 5,152,994 A | 10/1992 | Lotsof |
| 5,283,247 A | 2/1994 | Dwivedi et al. |
| 5,290,784 A | 3/1994 | Qu et al. |
| 5,316,759 A | 5/1994 | Rose et al. |
| 5,382,657 A | 1/1995 | Karasiewicz et al. |
| 5,426,112 A | 6/1995 | Zagon et al. |
| 5,552,406 A | 9/1996 | Mendelson et al. |
| 5,574,052 A | 11/1996 | Rose et al. |
| 5,578,645 A | 11/1996 | Askanazi et al. |
| 5,580,876 A | 12/1996 | Crain et al. |
| 5,591,738 A | 1/1997 | Lotsof |
| 5,616,575 A | 4/1997 | Efange et al. |
| 5,618,555 A | 4/1997 | Tokuda et al. |
| 5,703,101 A | 12/1997 | Rose et al. |
| 5,726,190 A | 3/1998 | Rose et al. |
| 5,760,044 A | 6/1998 | Archer |
| 5,861,422 A | 1/1999 | Rose et al. |
| 5,865,444 A | 2/1999 | Kempf et al. |
| 5,925,634 A | 7/1999 | Olney |
| 5,935,975 A | 8/1999 | Rose et al. |

(Continued)

FOREIGN PATENT DOCUMENTS

| | | |
|---|---|---|
| CA | 2039197 | 9/1995 |
| DE | 22 17 132 | 10/1972 |

(Continued)

OTHER PUBLICATIONS

"Analysis—HPLC—Interchim technology", Interchim.com, pp. B31-B93.

Ala-Hurula, et al. "Erogotamine Abuse: Results of Ergotamine Discontinuation, with Special Reference to the Plasma Concentrations," Cephalalgia, 2:4 1982, abstract only.

Ala-Hurula, et al. "Tolfenamic Acid and Ergotamine Abuse," Headache, 21:6, 1981, abstract only.

Alexander. "A Procedure for Drug Screening Without the Need to Transport Urines Use of Ion Exchange Papers and Hem Agglutination Inhibition," Clinical Toxicology, 9:3, 1976, abstract only.

Alim, et al. "Open-Label, Dose Run-Up Study of Diethylpropion in Initial Cocaine Abstinence," Clinical Neuropharmacology, 17:2, 1994, abstract only.

Almeida. "Use and Abuse of Alcohol and Drugs a Clinical Study of Certain Aspects of Their Interrelationship," Boletin de la Oficina Sanitaria Panamericana, 88:1, 1980, abstract only.

(Continued)

*Primary Examiner* — Peter D Mulcahy
*Assistant Examiner* — Henry Hu
(74) *Attorney, Agent, or Firm* — Foley & Lardner LLP

(57) ABSTRACT

Disclosed are methods and compositions for purifying the non-addictive alkaloid noribogaine.

5 Claims, No Drawings

(56) References Cited

U.S. PATENT DOCUMENTS

| | | | |
|---|---|---|---|
| 6,211,360 B1 | 4/2001 | Glick et al. | |
| 6,291,675 B1 | 9/2001 | Coop et al. | |
| 6,348,456 B1 * | 2/2002 | Mash | C07D 487/22 514/214.03 |
| 6,451,806 B2 | 9/2002 | Farrar | |
| 6,806,291 B1 | 10/2004 | Sunkel et al. | |
| 6,864,271 B2 | 3/2005 | Bazan et al. | |
| 7,220,737 B1 * | 5/2007 | Mash | A61K 31/397 514/210.05 |
| 7,737,169 B2 * | 6/2010 | Corrie | C07D 209/08 514/415 |
| 7,745,479 B2 * | 6/2010 | Nettekoven | C07D 401/12 514/217.04 |
| 8,017,151 B2 | 9/2011 | Batrakova et al. | |
| 8,178,524 B2 | 5/2012 | Mash | |
| 8,362,007 B1 * | 1/2013 | Mash | A61K 31/55 514/214.02 |
| 8,637,648 B1 | 1/2014 | Mash et al. | |
| 8,741,891 B1 | 6/2014 | Mash | |
| 8,765,737 B1 * | 7/2014 | Mash | C07D 471/22 514/214.02 |
| 8,802,832 B2 | 8/2014 | Mash et al. | |
| 2003/0153552 A1 | 8/2003 | Mash et al. | |
| 2003/0158202 A1 | 8/2003 | Caldirola et al. | |
| 2006/0051317 A1 | 3/2006 | Batrakova et al. | |
| 2007/0185085 A1 | 8/2007 | Mash | |
| 2010/0311722 A1 | 12/2010 | Mash | |
| 2010/0311723 A1 | 12/2010 | Mash | |
| 2010/0311724 A1 | 12/2010 | Mash | |
| 2010/0311725 A1 | 12/2010 | Mash | |
| 2012/0083485 A1 | 4/2012 | Mash | |
| 2012/0253037 A1 | 10/2012 | Moriarty et al. | |
| 2013/0072472 A1 * | 3/2013 | Gless, Jr. | C07D 471/22 514/214.02 |
| 2013/0131046 A1 | 5/2013 | Moriarty et al. | |
| 2013/0165647 A1 | 6/2013 | Moriarty et al. | |
| 2013/0303756 A1 | 11/2013 | Mash et al. | |
| 2014/0187655 A1 | 7/2014 | Mash et al. | |
| 2014/0315837 A1 | 10/2014 | Mash et al. | |
| 2014/0315891 A1 | 10/2014 | Mash | |
| 2014/0357741 A1 | 12/2014 | Mash et al. | |

FOREIGN PATENT DOCUMENTS

| | | |
|---|---|---|
| EP | 2 338 494 | 6/2011 |
| GB | 0 841 697 | 7/1960 |
| GB | 0 924 042 | 4/1962 |
| GB | 1 256 914 | 12/1971 |
| GB | 1 378 348 | 12/1974 |
| GB | 2 271 059 | 4/1994 |
| JP | 04-221315 | 8/1992 |
| WO | WO-91/18609 A1 | 12/1991 |
| WO | WO-93/20825 A1 | 10/1993 |
| WO | WO-93/25217 A1 | 12/1993 |
| WO | WO-94/06426 A1 | 3/1994 |
| WO | WO-94/14490 A1 | 7/1994 |
| WO | WO-96/01327 A1 | 1/1996 |
| WO | WO-96/03127 A1 | 2/1996 |
| WO | WO-99/11250 | 3/1999 |
| WO | WO-2007/012464 | 2/2007 |
| WO | WO-2007/070892 | 6/2007 |
| WO | WO-2012/012764 A1 | 1/2012 |
| WO | WO-2013/065850 | 5/2013 |
| WO | WO-2013/085850 | 6/2013 |
| WO | WO-2013/085922 A1 | 6/2013 |
| WO | WO-2013/148572 | 10/2013 |

OTHER PUBLICATIONS

Al-Shabanah, et al. "Gastric Antiulcer and Cytoprotective Effects of Cathinone, a Psychoactive Alkaloid of Khat (Catha Edulis Forsk.) and Amphetamine in Rats," Regulatory Peptides, abstract only, 1994.
Azevedo, et al. "Adrenergic Nerve Degeneration Induced by Condensation Products of Adrenaline and Acetaldehyde," Naunyn-Schmiedeberg's Archives of Pharmacology, 300:2, 1977, abstract only.
Bagal, et al. "Modulation of Morphine-Induced Antinociception by Ibogaine and Noribogaine," Brain Research, 741:1-2, 1996, pp. 258-262.
Bartlett, et al. "The Alkaloids of Tabernanthe iboga. Part IV. The Structures of Ibogamine, Ibogaine, Tabernanthine and Voacangine." Journal of the American Chemical Society, 80, 1958, pp. 126-136.
Batrakova. "Pluronic P85 Enhances the Delivery of Digoxin to the Brain: In Vitro and In Vivo Studies", The Journal of Pharmacology and Experimental Therapy, 296, 2001, pp. 551-557.
Baumann et al. "Comparative Neurobiology of Ibogaine and its Metabolite, 12-Hydroxyibogaimine (Noribogaine), in Rodents." Conference at New York University, Abstract only.
Beaubrun. "The Diagnosis and Management of Acute Psychotic Reaction Due to Alcohol and Drugs", Caribbean Medical Journal, 36:1, 1975, abstract only.
Beck, et al. "Energy-Dependent Reduced Drug Binding as a Mechanism of Vinca Alkaloid Resistance in Human Leukemic Lymphoblasts", Molecular Pharmacology, 24:3, 1983, abstract only.
Benet et al. "Pharmacokinetics: Biotransformation of Drugs." In Gilman et al. Goodman and Gilman's the Pharmacological Basis of Therapeutics (1990) :13-16.
Benoist, et al. "Comparative Effects of Fagaronine Adriamycin and Aclacinomycin on K562 Cell Sensitivity to Natural-Killer-Mediated Lysis Lack of Agreement Between Alteration of Transferrin Receptor and CD15 Antigen Expressions and Induction of Resistance to Natural Killer", Cancer Immunology Immunotherapy , 30:5, 1989, abstract only.
Bert, et al. "Non-Amphetaminic Central Stimulation by Alkaloids from the Ibogaine and Vobasine Series", Planta Medicina, 54:3, 1988, abstract only.
Bhargava, et al. "Effects of ibogaine and noribogaine on the antinociceptive action of mu-, delta- and kappa-opioid receptor agonists in mice", Brain Research 752, 1997, pp. 234-238.
Blum, et al. "Peyote a Potential Ethnopharmacologic Agent for Alcoholism and Other Drug Dependencies Possible Biochemical Rationale", Clinical Toxicology, 11:4, 1977, abstract only.
Blum, et al. "Possible Role of Tetrahydroisoquinoline Alkaloids in Postalcohol Intoxication States", Annals of the New York Academy of Science, 273, 1976, abstract only.
Blum, et al. "Putative Role of Isoquinoline Alkaloids in Alcoholism: A Link to Opiates", Alcoholism: Clinical and Experimental Research, 2:2, 1978, abstract only.
Brady, et al. "Analgesic Effects of Intraventricular Morphine and Enkephalins in Nondependent and Morphine-Dependent Rats," Journal of Pharmacology and Experimental Therapy, 222:1, 1982, abstract only.
Buchi, et al. "The total synthesis of iboga alkaloids," Jounal of the American Chemical Society, 88, 1966, pp. 3099-3109.
Bundgaard. "Design of Prodrugs: Bioreversible Derivatives for Various Functional Groups and Chemical Entities." Design of Prodrugs, 1-10, 1985.
Bussel, et al. "Isolated Thrombocytopenia in Patients Infected with HIV Treatment with Intravenous Gamma Globulin," American Journal of Hematology, 28:2, 1988, abstract only.
Caldwell, et al. "The Biochemical Pharmacology of Abused Drugs. III. Cannabis, Opiates, and Synthetic Narcotics," Clinical Pharmacological Therapy, 16:6, 1974, abstract only.
Cankat. "Pharmacological Aspects of Drug Induced Headache", Functional Neurology, 7:6, 1992, abstract only.
Cappendijk, et al. "The Inhibitory Effect of Norharman on Morphine Withdrawal Syndrome in Rats: Comparison with Ibogaine." Behavioural Brain Research, 65, 1994, pp. 117-119.
Cappendijk, et al. "Inhibitory Effects of Ibogaine on Cocaine Self-Administration in Rats", European Journal of Pharmacology, 241:2-3, 1993, abstract only.
Castle. "Drugs and Fibrotic Reactions—Part I", Adverse Drug React. Bull., 113: abstract only, 1985.
Chemical abstract, RN 16671-16-2 Registry, 1967.
Chemical abstract, RN 3464-63-9 Registry, 1965.
Chemical abstract, RN 481-87-8 Registry, 1952.
Chemical abstract, RN 4865-78-5 Registry, 1965.
Chemical abstract, RN 53508-36-4 Registry, 1974.
Chemical abstract, RN 57511-56-5 Registry, 1975.

(56) References Cited

OTHER PUBLICATIONS

Chemical abstract, RN 77123-15-0 Registry, 1980.
Chemical abstract, RN 83-74-9 Registry, 1934.
Chemical abstract, RN 88660-07-5 Registry, 1983.
Chemical abstract, RN 88660-09-7 Registry, 1983.
Cherny, et al., Opioid responsiveness of cancer pain syndromes caused by neuropathic or nociceptive mechanisms: a combined analysis of controlled, single-dose studies, Neurobiology 44, 1994, pp. 857-861.
Cheze, et al. "Determination of ibogaine and noribogaine in biological fluids and hair by LC-MS/MS after Tabernanthe iboga abuse", Forensic Science International, Elsevierscientific Publishers Ireland Ltd, IE, vol. 176, No. 1, Nov. 19, 2007, pp. 58-66.
Criel, et al. "Drug Dependent Red Cell Antibodies and Intravascular Haemolysis Occurring in Patients Treated with 9 Hydroxy-Methyl-Ellipticinium," British Journal of Haematology, 46:4, 1980, abstract only.
Damstrup, et al. "Retroperitoneal Fibrosis After Long-Term Daily Use of Ergotamine," International Urology and Nephrology, 18:3, 1986, abstract only.
Database Registry (Online), Chemical Abstracts Service, Columbus Ohis, US Nov. 16, 1984, "ibogamine-18-carboxylic acid, 12-methoxy-,potassium sal," XP002638006, Database accession No. 5500-12-9.
Database Registry Chemical Abstracts Service, Columbus, Ohio, US; 1984, "Ibogamine-18-carboxylic acid, 12-methoxy-, potassium sal", Database accession No. 5500-12-9.
Deecher, et al. "Mechanisms of Action of Ibogaine and Harmaline Congeners Based on Radioligand Binding Studies." Brain Research 571, 1992, pp. 242-247.
Diener, et al. "Analgesic-Induced Chronic Headache Long-Term Results of Withdrawal Therapy," Journal of Neurology, 236:1, 1989, abstract only.
Dierckx, et al. "Intraarterial Sodium Nitroprusside Infusion in the Treatment of Severe Ergotism," Clinical Neuropharmacology, 9:6, 1986, abstract only.
Dzoljic, et al. "Effect of Ibogaine on Naloxone-Precipitated Withdrawal Syndrome in Chronic Morphine-Dependent Rats," Archives Internationales de Pharmacodynamie et de Thérapie, 294, 1988, pp. 64-70.
Eberwine, et al. "Molecular Analysis of Cellular Responses to Opiate Use", Fidia Research Foundation Symposium Series 7 (Neurotransmitter Regulation of Gene Transcription) 1991, abstract only.
Elkind. "Drug Abuse and Headache", Medical Clinics of North America, 75:3, 1991, abstract only.
Evenson. "Developments in Therapeutic Drug Monitoring and Alkaloid Analysis", Federation Proceedings, 34:12, 1975, abstract only.
Extended European Search Report dated Jun. 6, 2011 in related European Patent Appl. No. 11159572.4.
Faglia, et al. "Dihydroergocryptine in Management of Microprolactinomas," Journal of Clinical Endocrinology & Metabolism, 65:4, 1987, abstract only.
Fairchild, et al. "Keynote Address: Multidrug Resistance: A Pleiotropic Response to Cytotoxic Drugs," International Journal of Radiation, Oncology, Biology, & Physics, 20:2, 1991, abstract only.
Finkle. "Phencyclidine Identification by Thin-Layer Chromatography. A Rapid Screening Procedure for Emergency Toxicology", American Journal of Clinical Pathology, 70:2, 1978, abstract only.
Fonne-Pfister, et al. "Xenobiotic and Endobiotic Inhibitors of Cytochrome P-450db1 Function, the Target of the Debrisoquine / Sparteine Type Polymorphism," Biochemical Pharmacology, 37:20, 1988, abstract only.
Frances, et al. "Effects of Ibogaine on Naloxone-Precipitated Withdrawal in Morphine-Dependent Mice", Fundamental Clininical Pharmacology, 6:8-9, 1992, abstract only.
Gabr, et al. "Changes in Absolute Amount of Alkaloids in Datura-Metel Treated with Certain Growth Regulators", Herba Pol, 21:2, 1975, abstract only.

Garcia, et al. Chronic pain states: pathophysiology and medical therapy, Seminars in Arthritis and Rheumatism, 27, 1997, pp. 1-16.
Gennaro. "Remington: The Science and Practice of Pharmacy", Mack Publishing Col., vol. II, 1995, pp. 1736 & 1814.
George, et al. "Palliative medicine", Postgraduate Medical Journal, vol. 69, 1993, pp. 426-449.
Gifford, A. N. and Johnson, K. Gifford, et al. "Effect of Chronic Cocaine Treatment on D SUB 2 Receptors Regulating the Release of Dopamine and Acetylcholine in the Nucleus Accumbens and Striatum", Pharmacology, Biochemistry and Behavior, 41:4, 1992, abstract only.
Glick, et al. "Effects of iboga Alkaloids on Morphine and Cocaine Self-Administration in Rats: Relationship to Tremorigenic Effects and to Effects on Dopamine Release in Nucleus Accumbens and Striatum." Brain Research, 657, 1994, pp. 14-22.
Glick, et al. "Effect of Ibogaine on Acute Signs of Morphine Withdrawal in Rats: Independence from Tremor", Neuropharmacology, 31:5, 1992, abstract only.
Glick, et al. "Effects of Aftereffects of Ibogaine on Morphine Self-Administration in Rats", European Journal of Pharmacology, 195:3, 1991, abstract only.
Glick, et al. "Ibogaine-like effects of noribogaine in rats", Brain Research, 713, 1996, pp. 294-297.
Glick, et al. "Local Effects of Ibogaine on Extracellular Levels of Dopamine and Its Metabolites in Nucleus Accumbens and Striatum: Interactions with D-Amphetamine", Brain Research, 628:1-2, 1993, abstract only.
Gold, et al. "Effect of Methadone Dosage on Clonidine Detoxification Efficacy", American Journal Psychiatry, 137:3, 1980, abstract only.
Gothoni. "Harmine-, Lon-954- and 5-Hydroxytryptophan-Induced Tremors in Rats Withdrawn from Ethanol", Acta Pharmacologica et Toxicologica, Copenhagen, DK, 57:1, 1985, abstract only.
Greenwald, et al., "Poly(ethylene glycol) conjugated drugs and prodrugs: a comprehensive review," Crit. Rev. Ther. Drug Carrier Syst., (2000), 17(2):101-161.
Gross. "Effect of Ergot Alkaloids on Serum Prolactin in Non-Psychotic Organic Brain Syndrome of the Elderly", Experimental Aging Research, 5:4, 1979, abstract only.
Gunn. "Relations Between Chemical Constitution, Pharmacological Actions, and Therapeutic Uses, in the Harmine Group of Alkaloids." From the Pharmacological Laboratory, University of Oxford, 1935, pp. 379-396.
Haber, et al. "Tetrahydroisoquinolines—Endogenous Products After Chronic Alcohol Abuse", Pharmazie, 47:1, 1992, abstract only.
Halikas, et al. "Treatment of Crack Cocaine Use with Carbamazepine", American Journal of Drug and Alcohol Abuse, 18:1, 1992, abstract only.
Hanks. "Opioid-responsive and opioid-non-responsive pain in cancer," British Medical Bulletin 47, 1991, pp. 718-731.
Hardman, et al. "Goodman & Gilman's The Pharmacological Basis of Therapeutics" (9th ed, 1996) p. 51 and pp. 57-58.
Harsing, et al. "Evidence that Ibogaine Releases Dopamine from the Cytoplasmic Pool in Isloated Mouse Striatum", Journal of Neural Transmission General Section, 96:3, 1994, abstract only.
Hearn, et al. "Identification and Quantitation of Ibogaine and an o-Demethylated Metabolite in Brain and Biological Fluids Using Gas Chromatography-Mass Spectrometry." Journal Analytical Toxicology, 19, 1995, pp. 427-434.
Heel, et al. "Buprenorphine: A Review of Its Pharmacological Properties and Therapeutic Efficacy", Drugs, 17:2, 1979, abstract only.
Henry, et al. "Reversible Cerebral Arteriopathy Associated with the Administration of Ergot Derivatives", Cephalalgia, 4:3, 1984, abstract only.
Ho, et al. "Metabolism of Harmaline in Rats." Biochemical Pharmacology vol. 20, 1971, pp. 1313-1319.
Hoes. "Clinical Criteria for the Selection of Anxiolytics", Tijdschrift voor Therapie Geneesmiddel en Onderzoek, 9:9, 1984, abstract only.
Holzner, et al. "The Neuroleptic Sleeping Course in Chronic Headache", Therapiewoche, 35/36: 1985, abstract only.

(56) References Cited

OTHER PUBLICATIONS

Huang, et al. "Cytotoxicity and Sister Chromatid Exchanges Induced in Vitro by Six Anticancer Drugs Developed in the People's Republic of China", Journal of the National Cancer Institute, 71:4, 1983, abstract only.
Hubens, et al. "Chronic Intake of a Hydrogenated Ergot Alkaloid Causing Peripheral Vascular Ischemia—A Case Report", Journal of Vascular Surgery, 21:4, 1987, abstract only.
Huffman et al., "A Formal Synthesis of (±)-Ibogamine," J. Org. Chem., (1985), 50:1460-1464.
Huffman, et al. "A Formal Synthesis of (±)-Ibogamine," Journal of Organic Chemistry, vol. 50, 1985, pp. 1460-1464.
International Preliminary Report on Patentability for PCT/US2012/067799, dated Jun. 19, 2014.
International Search Report and Written Opinion dated Mar. 11, 2013 in related PCT Patent Application No. PCT/US12/71052.
International Search Report and Written Opinion dated Oct. 4, 2012 in related PCT Application Serial No. PCT/US2012/022255.
International Search Report for PCT/US2011/045081 dated Oct. 4, 2011.
Isler. "Treatment of Headache", Schweizerische Medizinische Wochenschrift, 114:35, 1984, abstract only.
Jaffe. "Drug Addiction and Drug Abuse", in Gilman, et al., "Goodman and Gilman's The Pharmacological Basis of Therapeutics," New York, Pergamon Press, 1990, pp. 520-523 & pp. 559-568.
Jaffe. "Psychopharmacology and Opiate Dependence," U.S. Public Health Services Publication, 1957-1967: pp. 1836.
James. "Linkers for solid phase organic synthesis," Tetrahedron, 55, 1999, pp. 4855-4946.
Jane, et al. "High-Performance Liquid Chromatographic Analysis of Basic Drugs on Silica Columns Using Non-Aqueous Ionic Eluents. II. Application of UV, Fluorescence and Electrochemical Oxidation detection", Journal of Chromatography, 323:2, 1985, abstract only.
Jansen, et al. "Ethnopharmacology of Kratom and the Mitragyna Alkaloids", Journal of Ethnopharmacology, 23:1, 1988, abstract only.
Janzen. "History of Use of Psychotropic Drugs in Central Africa," Psychotropes, 1/2: 1983, abstract only.
Justins. "Management strategies for chronic pain," Annals of the Rheumatic Diseases, vol. 55, 1996, pp. 588-596.
Kalix. "Khat: A Plant with Amphetamine Effects," Journal of Substance Abuse Treatment, 5:3, 1988, abstract only.
Kalix. "Pharmacological Properties of the Stimulant Khat", Pharmacological Therapy, 48:3, 1990, abstract only.
Keefner. "A Gas Chromatography-Mass Spectrometry (GCMS) Method for Ibogaine", Society for Neuroscience Abstracts, 19:1-3, 1993, abstract only.
Keller, et al. "Modulation of Neopterin Release by Human Kupffer Cells in Culture: Possible Implication in Clinical Monitoring of HIV-Seropositive Subjects", Cells Hepatic Sinusoid, 3: 1991, abstract only.
Knoll. "Azidomorphines and Homopyrimidazols: A New Approach to the Ideal Analgetic," ACTA Physiologica et Pharmacologica Bulgarica, 3:2, 1977, abstract only.
Knoll. "Azidomorphines: A New Family of Potent Analgesics with Low Dependence Capacity," Progress in Neuro-Psychopharmacology and Biological Psychiatry, 3:1-3, 1979, abstract only.
Koch, et al. "Drug-Induced Liver Injury in Liver Biopsies of the Years 1981 and 1983, their Prevalence and Type of Presentation", Pathology, Research and Practice, 179: 1985, abstract only.
Konig. "Psychiatric Intensive Therapy After Acute Alkaloid Withdrawal Syndrome", Infusionsther Klin Ernahr, 6:1, 1979, abstract only.
Kornetsky. "Pharmacology Drugs Affecting Behavior." John Wiley & Sons, 1976, pp. 185-187.
Kostowski, et al. "The Effects of Some Hallucinogens on Aggressiveness of Mice and Rats" Pharmacology, 7, 1972, pp. 259-263.
Krug. "Cocaine Abuse: Historical, Epidemiologic, and Clinical Perspectives for Pediatricians", Advances in Pediatrics, 36:369-406, 1989.

Kupers, et al. "Morphine differentially affects the sensory and affective pain ratings in neuorgenic and idiopathic forms of pain." Pain, 47, 1991, pp. 5-12.
Lakoski, et al. "Electrophysiologic Characterization of an Ibogaine Metabolite in Dorsal Raphe Nucleus and Hippocampus." Society for Neuroscience, 21:716, 1995, abstract only.
Larson-Prior, et al. "Electrophysiologic Characterization of an Ibogaine Metabolite in the Cerebellar Cortex." Society for Neuroscience, 21:716, 1995, abstract only.
Layer, et al., "Structurally modified ibogaine analogs exhibit differing affinities for NMDA receptors," European Journal of Pharmacology, 1996, 309:159-165.
Lemontt, et al. "Increase MDR Gene Expression and Decreased Drug Accumulation in Multidrug-Resistant Human Melanoma Cells", Cancer Research, 48:22, 1988, abstract only.
Leoni, et al. "Effect of Cocaine and Morphine on Neutral Endopeptidase Activity of Human Peripheral Blood Mononuclear Cells Cultures with Lectins," Cell Biochemistry and Function, 11:3, 1993, abstract only.
Lerida, et al. "Incidence of Morphine Withdrawal and Quasi-Abstinence Syndrome in a Model of Chronic Pain in the Rat," Neuroscience, 81:1-2, 1987, abstract only.
Lewis, et al. "Adverse Reactions and Interactions with .beta.-Adrenoceptor Blocking Drugs," Journal of Medical Toxicology, 1:5, 1986, abstract only.
Lewis, et al. "Narcotic Analgesics and Antagonists," Annual Review of Pharmacology, 11, 1971, abstract only.
Licht, et al. "Induction of Multiple-Drug Resistance During Anti-Neoplastic Chemotherapy In-Vitro," International Journal of Cancer, 49:4, 1991, abstract only.
Ling, et al. "Drugs of Abuse-Opiates", in Addtiction Medicine [Special Issue], Western Journal of Medicine, 152, 1990, pp. 565-572.
Low, et al. "Effects of Acronycine and Cytouchalasin B on the Division of Rat Leukemia Cells," Experimental Cell Research, 131:1, 1981, abstract only.
Ma, et al. "Inhibition of Respiratory Burst Activity in Alveolar Macrophages by Bisbenzylisoquinoline Alkaloids: Characterization of Drug-Cell Interaction", Experimental Lung Research, 18:6, 1992, abstract only.
Maisonneuve, et al. "Interactions of Ibogaine and D-Amphetamine: in vivio Microdialysis and Motor Behavior in Rats." Brain Research 579, 1992, pp. 87-92.
Maisonneuve, et al. "Acute and Prolonged Effects of Ibogaine on Brain Dopamine Metabolism and Morphine-Induced Locomotor Activity in Rats", Brain Research, 575:1, 1992, abstract only.
Maisonneuve, et al. "Interactions Between Ibogaine, a Potential Anti-Addictive Agent, and Morphine: an in Vivo Microdialysis Study," European Journal of Pharmacology, 199:1, 1991, abstract only.
Martellotta, et al. "Effects of the Calcium Antagonist Isradipine on Cocaine Intravenous Self-Administration in Rats", Psychopharmacologia, 113:3-4, 1994, abstract only.
Martin, et al. "Neuropathic Pain in Cancer Patients: Mechanisms, Syndromes, and Clinical Controversies," Journal of Pain and Symptom Management, 14:2, 1997, pp. 99-117.
Mash, et al. "Ibogaine in the Treatment of Heroin Withdrawal," The Alkaloids 56, 2001, pp. 1-17.
Mash, et al. "Ligand Binding Profiles of Ibogaine and its O-demethylated Metabolite Noribogaine: Implications for Developing Novel Multi-target Anti-addiction Agents." Society of Neurosciences, vol. 21, 1995, abstract only.
Mash, et al. "Preclinical screening of an ibogaie metabolite (noribogaine) on cocaine-induced hyperlocomotion and cocaine self-administration." Society of Neurosciences, vol. 22, 1996, abstract only.
Mash, et al. "Properties of Ibogaine and its Principle Metabolite (12-hydroxyibogamine) at the MK-801 binding site of the NMDA receptor complex," Neuroscience Letters, 192, 1995, pp. 53-56.
Mateer, et al. "Reversible Ipecac Myopathy," Archives of Neurology, 42:2, 1985, abstract only.
Matharu, et al. "Preformulation and Development of Ibogaine Injection for the Treatment of Drug Abuse," Pharmaceutical Research, 10: 1993, abstract only.

(56) References Cited

OTHER PUBLICATIONS

Mattingly, et al. "Selective Antagonism of Dopamine D Sub 1 and D Sub 2 Receptors Does Not Block the Development of Behavioral Sensitization to Cocaine," Psychopharmacologia, 114:2, 1994, abstract only.
McNeish, et al. "The 5-HT Sub 3 Antagonist Zacopride Attenuates Cocaine-Induced Increases in Extracellular Dopamine in Rat Nucleus Accumbens," Pharmacology, Biochemistry, and Behavior, 45:4, 1993, abstract only.
Melchior, et al. "Preference for Alcohol Evoked by Tetra Hydro Papaveroline Chronically Infused in the Cerebral Ventricle of the Rat," Pharmacol Biochem Behav, 7:1, 1977, abstract only.
Mendelson & Mello "Cocaine and Other Commonly Abused Drugs," In Isselbacher et al. (ed.), "Harrison's Principals of Internal Medicine." 13th Ed., McGraw-Hill Inc., 1994, pp. 2429-2433.
Mendelson, et al. "Cocaine and Other Commonly Abused Drugs." In Isselbacher et al. "Harrison's Principles of Internal Medicine." 1994, pp. 2429-2433.
Menzies, et al. "Gangrene of the Small Bowel: A Complication of Methysergide Therapy," Australian and New Zealand Journal of Surgery, 52:5, 1982, abstract only.
Metelitsa. "Pharmacological Agents in Controlling Smoking," Biull Vsesoiuznogo Kardiol Nauchn Tsentra, 10:1, 1987, abstract only.
Millan. "k-Opioid Receptors and Analgesia," Trendes in Pharmacologicla Sciences, 11, 1990, pp. 70-76.
Mizuhashi, et al. "Antitumor Activities of IKP-104 A 4-1H Pyridizinone Derivative on Cultured and Implanted Tumors," Japanese Journal of Cancer Research, 81:12, 1990, abstract only.
Montefiori, et al. "In Vitro Evaluation of Mismatched Double-Stranded RNA (Ampligen) for Combination Therapy in the Treatment of Acquired Immunodeficiency Syndrome," AIDS Research and Human Retroviruses, 5:2, 1989, abstract only.
Mulamba et al., "Alkaloids from tabernanthe pubescens", Journal of Natural Products, 44(2):184-189, 1981.
Mulamba et al., Alcaloids de Tabernanthe Pubescens. Journal of Natural Products, (1981), 44:(2):184-189.
Naranjo. "Ibogaine in psychotherapy: psychoanalysis according to Naranjo", part IV, pp. 1-2. http://www.nettuno.it/fiera/electric.italy/bwitif:html.
Niemann et al, "The Isolation of Rupicoline and Montanine, Two Pseudoindoxyl Alkaloids of Tabernaemontana Rupicola Benth", The Journal of Organic Chemistry, 31(7):2265-2269.
Nishiyama, et al. "Expression of the Multidrug Transporter, P-Glycoproteiin, in Renal and Transitional Cell Carcinomas," Cancer, 71:11, 1993, pp. 3611-3619.
Nooter, et al. "Multidrug Resistance (MDR) Genes in Haematological Malignancies," Cytotechnology, 12:1-3, 1993, abstract only.
Nunn-Thompson, et al. "Pharmacotherapy for Making Cessation", Clin Pharm, 8:10, 1989, abstract only.
Obach, et al., "Cythochrome P4502D6 Catalyzes the O-Demethylation of the Psychoactive Alkaloid Ibogaine to 12-Hydroxyibogamine," Drug Metabolism and Disposition 26:8, 1998, pp. 764-768.
O'Hearn, et al. "Degeneration of Prukinje Cells in Parasagittal Zones of the Cerebellar Vermis After Treatment with Ibogaine of Harmaline," Neuroscience, 55:2, 1993, abstract only.
O'Hearn, et al. "Ibogaine Induces Glial Activation in Parasagittal Zones of the Cerebellum," Neuroreport, 4:3, 1993, abstract only.
Pablo, et al, "Noribogaine Stimulates Naloxone-Sensitive[35S]GTPgammaS Binding," NeuroReport, 9, 1998, pp. 109-114. (Website Publication Date of Dec. 20, 1997.).
Pacifici , et al. "Immunological Effect of Cocaine and Host Resistance in Mice," International Journal of Immunotherapy, 8:2, 1992, abstract only.
Palyi. "Survivial Responses to New Cytostatic Hexitols of P388 Mouse and K562 Leukemia Cells in Vitro," Cancer Treatment Reports, 70:2, 1986, abstract only.
Pantazis, et al. "Efficacy of Camptothecin Congeners in the Treatment of Human Breast Carcinoma Xenografts," Oncology Research, 5:8, 1994, abstract only.

PCT International Preliminary Report on Patentability dated Jul. 30, 2013 in related PCT International Patent Application No. PCT/US2012/022255.
Pehek. "Effects of Cathinone and Amphetamine on the Neurochemistry of Dopamine in Vivo," Neuropharmacology, 29:12, 1990, abstract only.
Perera, et al. "Tertiary Indole Alkaloids of Tabernaemontana Dichotoma Seeds," Planta Medica, 49:1, 1983, abstract only.
Perrin. "Clinical Pharmacokinetics of Ergotamine in Migraine and Cluster Headache," Clinical Pharmacokinetics, 10:4, 1985, abstract only.
Popik, et al. "NMDA Antagonist Properties of the pUtative Antiaddictive Drug, Ibogaine," Journal of Pharmaceutical and Experimental Therapeutics, 275:2, 1995, pp. 753-760.
Popik, et al. "The Putative Anti-Addictive Drug Ibogaine is a Competitive Inhibitor of (SUP 3 H) Binding to the NMDA Receptor Complex", Psychopharmacologia, 114:4, 1994, abstract only.
Popik, et al. "100 Years of Ibogaine: Neurochemical and Pharmacological Actions of a Putative anti-addictive Drug," Pharmacological Reviews 47:2, 1995, pp. 235-253.
Pulvirenti, et al. "Lisuride Reduces Intravenous Cocaine Self-Administration in Rats," Pharmacology, Biochemistry and Behavior, 47:4, 1994, abstract only.
Qiu, et al. "The Influence of Chronic Nicotine Treatment on Stress-Induces Gastric Ulceration and Emptying Rate in Rats," Experientia, 48:4, 1992, abstract only.
Radouco-Thomas, et al. "Adverse effects to Psychotomimetics. Proposition of a Psychopharmacological Classification." Pharmacologie, Toxicologie, et abus des psychotomimetiques (hallucinogens), 109, 1974, abstract only.
Rezvani, et al. "Noribogaine, a Primary Ibogaine Metabolite, Reduces Alcohol Intake in P and Fawn-Hooded Rats." RSA Annual Scientific Meeting, 1995, abstract only.
Rezvani, et al. "Reduction of Alcohol Intake in Alcohol Preferring Fawn-hooded and P Rats by Noribogaine, the Primary Metabolite of Ibogaine." NIDA Monograph Series 162:281, 1996, Abstract only.
Ricceri, et al. "Postnatal cocaine Esposure Affects Neonatal Passive Avoidance Performance and Cholinergic Development in Rats," Pharmacology, Biochemistry and Behavior, 45:2, 1993, abstract only.
Rodriguez, et al. "Cocaine Adminstration Prior to Reactivation Facilitates Later Acquisition of an Avoidance Response in Rats," Psychopharmacologia, 112:2-3, 1993, abstract only.
Rosenmund, et al. "Ibogamin, Ibogain and Epiibogamin" Chemische Berichte, 108, 1975, pp. 1871-1895.
Sachs, et al. "Corneal Complications Associated with the Use of Crack Cocaine," Ophthalmology, 100:2, 1993, abstract only.
Salmoiraghi, et al. "Effects of LSD 25, BOL 148, Bufotenine, Mescaline and Ibogaine on the Potentiation of Hexobarbital Hypnosis Produced by Serotonin and Reserpine." Journal of Pharmacology and Experimental Therapeutics 120:1, 1957, pp. 20-25.
Samadi-Baboli, et al. "Preparation of Low Density Lipoprotein-9-Methoxy-Illipticin Complex and Its Cytotoxic Effect Against L1210 and P 388 Leukemic Cells in Vitro," European Journal of Cancer and Clinical Oncology , 25:2, 1989, abstract only.
Saper, et al. "Ergotamine Tartrate Dependency: Features and Possible Mechanisms," Clinical Neuropharmacology, 9:3, 1986, abstract only.
Schecter, et al. "Comparison of the Behavioral Effects of Ibogaine from Three Sources: Mediation of Discriminative Activity," European Journal of Pharmacology, 249:1, 1993, abstract only.
Schneider, et al. "Analysis of the Cardiovascular Action of Ibogaine Hydrochloride." Archives Internationales de Pharmacodynamie et de Thérapie, 110, 1957, pp. 92-102.
Schneider, et al. "Neuropharmacological Studies of Ibogaine: An Indole Alkaloid with Central Stimulant Properties." Annals of the New York Academy of Sciences, 66, 1957, pp. 765-776.
Schneider, et al., "Potentiation Action of Ibogaine on Morphine Analgesia" Experiential, 12, 1956, pp. 323-324.
Schnider, et al. "Use and Abuse of Analgesics in Tension-Type Headache," Cephalalgia, 14:2, 1994, abstract only.
Schuckit & Segal. "Opiod Drug Use," In Isselbacher et al. (ed.), "Harrison's Principals of Internal Medicine." 13th Ed., McGraw-Hill Inc., 1994, 2425-2429.

(56) References Cited

OTHER PUBLICATIONS

Schuckit. "Alcohol and Alcoholism," In Isselbacher et al. (ed.), "Harrison's Principals of Internal Medicine." 13th Ed., McGraw-Hill Inc., 1994, pp. 2420-2425.
Seeber, et al. "In Vivo Resistance Towards Anthracyclines, Etoposide, and Cis-Diamminedichloroplatinum (II)," Cancer Research, 42:11, 1982, abstract only.
Sehested, et al. "The Carboxylic Ionophore Monensin Inhibits Active Drug Efflux and Modulates In-Vitro Resistance in Daunorubicin Resistant Enrlich Ascites Tumor Cells," Biochemical Pharmacology, 37:17, 1988, abstract only.
Sershen, et al. "Ibogaine Antagonizes Cocaine-Induced Locomotor Stimulation in Mice," Life Sciences, 50:15, 1992, abstract only.
Sershen, et al. "Ibogaine Reduces Amphetamine-Induced Locomotor Stimulation in C57BL/6By Mice, but Stimulates Locomotor Activity in Rats," Life Sciences, 51:13, 1992, abstract only.
Sershen, et al. "Ibogaine Reduces Preference for Cocaine Consumption in C57BL/6By Mice," Pharmacology Biochemistry and Behavior, 47:1, 1994, abstract only.
Shen, et al. "Antagonists at Excitatory Opioid Receptors on Sensory Neurons in Culture Increase Potency and Specificity of Opiate Analgesics and Attenuate Development of Tolerance/ Dependence," Brain Research, 636:2, 1994, abstract only.
Sheppard. "A Preliminary Investigation of Ibogaine: Case Reports and Recommendations for Further Study." Journal of Substance Abuse Treatment, 11:4, 1994, abstract only.
Shir, et al. "Neuropathic pain unrelieved by morphine, alleviated by haloperidol," Harefuah 118:8, 1990, abstract only.
Shook et al. "A cyclic Somatostatin Analog that Precipitates Withdrawal in Morphine-Dependent Mice", NIDA Res. Monogr., 76(Probl. Drug Depend.): abstract only, 1987.
Sinkula, et al. "Rationale for Design for Biologically Reversible Drug Derivatives: Prodrugs." Journal of Pharmaceutical Sciences, 64:2, 1975, pp. 181-210.
Slotkin, et al. "A Model of Harmine Metabolism in the Rat." The Journal of Pharmacology and Experimental Therapeutics, 174:3, 1970, pp. 456-462.
Slotkin, et al. "Blood Levels and Urinary Excretion of Harmine and its Metabolites in Man and Rats." The Journal of Pharmacology and Experimental Therapeutics, 173:1, 1970, pp. 26-30.
Slotkin, et al. "Urinary Metabolites of Harmine in the Rat and their Inhibition of Monoamine Oxidase." Biochemical Pharmacology, 19, 1970, pp. 125-131.
Sloviter, et al. "A Common Mechanism of Lysergic Acid, Indolealkylamine and Phenethylamine Hallucinogens: Serotonergic Mediation of Behavioral Effects in Rats." Journal of Pharmacological Experimental Therapy, 214:2, 1980, pp. 231-238.
Smith. "Interaction of Biogenic Amines with Ethanol," Advances in Experimental Medicine and Biology, 56, 1975, abstract only.
Snyder, et al., "Practical HPLC Method Development", 1997, 2nd Ed., pp. 214-218, 266, 267, 282 & 283, John Wiley & Sons, Inc.
Solinas et. al., "Solid supported reagents and catch-and-release techniques in organic synthesis". Synthesis 20070816 DE LNKDDOI: 10.1055/S-2007-983806, No. 16., pp. 2409-2453, 2007.
Solinas, et al. "Solid-Supported Reagents and Catch-and-Release Techniques in Organic Synthesis", Synthesis 2007:16, 2007, pp. 2409-2453.
Stahl, et al., "Handbook of Pharmaceutical Salts", 1998, p. 250 John Wiley & Sons.
Stella. "Pro-drugs as Novel Drug Delivery Systems", ed. Higuchi, T. et al., American Chemical Society, Washington D.C., 1975, pp. 1-49.
Stella. "Pro-drugs: An Overview and Definition." Prodrugs as Novel Drug Delivery System. ACS Symposium Series: 1975, pp. 1-115.
Sugiyama, et al. "Quantitative Analysis of Cell-Kill Effects of Anticancer Drugs: Consideration of Both In Vitro and In Vivo Exprimental Systems." Gan To Kagaku Ryoho, 14:12, 1987, abstract only.
Tarnower, et al., "Ergotism Masquerading as Arteritis," Postgraduate Medicine, 85:1, 1989, abstract only.
Teoh, et al. "Buprenorphine Effects on Morphine- and Cocaine-Induced Subjective Responses by Drug-Dependent Men," Journal of Clinical Psychopharmacology, 14:1, 1994, abstract only.
Tfelt-Hansen, et al. "Nitroglycerin for Ergotism. Experimental Studies in Vitro and in Migraine Patients and Treatment of an Overt Case," European Journal of Clinical Pharmacology, 22:2, 1982, abstract only.
Torrenegra, et al. "Alkaloids of stemmadenia grandiflora", Phytochemistry, 27:6, 1988, pp. 1843-1848.
Tsuruo. "Multidrug Resistance: A Transport System of Antitumor Agents and Xenobiotics," Princess Takamatsu Symp, 21, 1990, abstract only.
Uldry, et al. "Cerebrovascular Accidents in Relation to Drug Consumption or Drug Abuse," Schweizerische Rundschau Fur Medizin Praxis, 78:23, 1989, abstract only.
Valadez, et al. "Persistence of the Ability of Amphetamine Preexposure to Facilitate Acquistion of Cocaine Self-Administration," Pharmacology, Biochemistry and Behavior, 47:1, 1994, abstract only.
Valencia, et al. "Obovatine, a New Bisindole Alkaloid from Stemmadenia Obovata," Journal of Natural Products, 58:1, 1995, pp. 134-137.
Vescovi, et al. "Successful Treatment of Opiate Withdrawal Using Lysine Acetylsalicylate," Current Therapeutic Research, Clinical and Experimental, 33:5, 1983, abstract only.
Villalba, et al. "Uses and Abuses of Ipecacuana Syrup", Farmacia Clinica, 9:1, 1992, abstract only.
Wells, et al. "Recognition and Treatment of Arterial Insufficiency from Cafergot," Journal of Vascular Surgury, 4:1, 1986, abstract only.
Whitaker, et al. "High Affinity 3H-Serotonin Binding to Caudate: Inhibition by Hallucinogenic and Serotonergic Drugs," Psychopharmacology 59, 1978, pp. 1-5.
Whitaker, et al. "Selective Labeling of Serotonin Receptors by d'(3H)Lysergic Acid Diethylamide in Calf Caudate." Proceedings of the National Academy of Sciences 75:12, 1978, pp. 5783-5787.
Whittaker, et al. "Recurrent Laryngeal Nerve Paralysis in Patients Receiving Vincristine and Vinblastine", British Medical Journal, 1:6071, 1977, abstract only.
Widler, et al. "Pharmacodynamics and Pharmacokinetics of Khat: a Controlled Study," Clinical Pharmacology Therapy, 55:5, 1994, abstract only.
Wildmann. "Heterocycles as Physiological Ligands for the Benzodiazepine Receptor and for Other Binding Sites", Pharmacology Residency, 21:6, 1989, abstract only.
Williams, et al. "The 'Alice in Wonderland' Experience Ergot Alkaloid Therapy for Prolactin-Secreting Pituitary Tumors," The Western Journal of Medicine, 138:3, 1983, abstract only.
Wishart, et al. "Is Multidrug Resistance Relevant in Breast Cancer," European Journal of Surgical Oncology, 17:5, 1991, abstract only.
Witt, et al. "Pharmacodynamic and Pharmacokinetic Characterization of Poly(Ethylene glycol) Conjugation to Met-Enkephalin Analog [D-Pen2,D-Pen5]-enkephalin (DPDPE)", Journal of Pharmcological and Experimental Therapy, 298:2, 2001, pp. 848-856.
Witt, et al. "Pluronic P85 Block Copolymer Enhances Opioid Pepetide Analgesia," Journal of Pharmcology and Experimental Therapy, 303:2, 2002, pp. 760-767.
Worz. "Effects and Risks of Psychotropic and Analgesic Combinations," American Journal of Medicine, 75:5A, 1983, abstract only.
Yang, et al., "Prodrug based optimal drug delivery via membrane transporter/receptor," Expert. Opin. Biol. Ther., (2001), 1(2):159-175.
Zetler, et al. "Pharmacokinetics in the Rat of the Hallucinogenic Alkaloids Harmine and Harmaline." Naunyn-Schmiedeberg's Archives of Pharmacology, 285, 1974, pp. 273-292.
Zetler, et al. "Cerebral Pharmacokinetics of Tremor-Producing Harmala and Iboga Alkaloids" Pharmacology, 7:4, 1972, pp. 237-248.
Buchi et al., "Chemical Transformations of Ibogaine," Journal of the American Chemical Society, 88:11, Jun. 5, 1966, pp. 2532-2535.
Extended European Search Report on EP Application 13740942.1, mailed Sep. 10, 2015.

(56) References Cited

OTHER PUBLICATIONS

Glick SD et al., Development of novel medications for drugs addiction. The legacy od an African shrub. AnnN.Y.Acad.Sci. 2000; 909:808-103 abstract[on-line] [found on Aug. 21, 2015]www.ncbi.nlm.nih.gov/pubmed/10911925.
International Search Report & Written Opinion for PCT/US2014/013063 dated Oct. 8, 2015.
JD Roberts, "Separation and Purification. Identification of Organic Compounds by Spectroscopic Techniques," Chapter 9, 1977 pp. 257-349.
Office Action on Russian Application 2013102923/15 dated Aug. 11, 2015 English translation provided.
Peterson, A. L. et al., Treatment of Parkinson's disease with trophic factors. Neurotherapeutics, 2008, vol. 5, No. 2, pp. 270-280.
RN:5500-12-9,Registry (STN) [online] , Nov. 16, 1984.
RN:766444-34-2,Registry (STN) [online], Oct. 20, 2004.
Wang et al., Targeted Delivery of GDNF through the Blood-Brain Barrier by MRI-Guided Focused Ultrasound, PLoS One, vol. 7, Issue 7, Article e52925, internal pp. 1-8, Dec. 2012.
Ahuja, Satinder (Ed.), "Chiral Separation Methods for Pharmaceutical and Biotechnological Products", John Wiley & Sons (published on line Oct. 2010).
Altman et al., "An Improved Cu-Based Catalyst System for the Reactions of Alcohols with Aryl Halides," J. Org. Chem., (2008), 73(1):284-286.
Baumann et al., In vivo Neurobiological Effects of Ibogaine and Its o-Desmethyl Metabolite, 12 Hydroxyibogamine (Noribogaine), in Rats, J. Pharmacol. Exp. Ther. 2001, vol. 297, No. 2, pp. 531-539.
Beesley et al., "Chiral Chromatography", John Wiley & Sons (1998).
Caccamese et al., "Chiral HPLC Separation and CD Spectra of the Enantiomers of the Alkaloid Tacamonine and Related Compounds", Chirality (2001), 13:691-93.
CALPUS printout of Watts et al. "Alkaloids from *stemmadenia* Species", I. Alkaloids of S. Donnellsmithiii and S. Galleottiana, (1958), vol. 2, pp. 173-182.
CALPUS printout of Zetler. "Some Pharmacological Properties of 12 Natural and 11 Partially Synthetic Indole Alkaloids from Tropical Apocyanaceae of the Subtribe Tabernaemontaninae", Arzneimittel-Forschung, (1964), 14:12, pp. 1277-1286.
CAS Registry record for "Noribogaine" (1984).
Chaturvedula et al, "New Cytotoxic Indole Alkaloids from Tabe rnaemontana calcarea from the Madagascar Rainforest", Journal of Natural Products, (2003), vol. 66, pp. 528-531.
Corey, E.J., "Catalytic Enantioselective Diels-Alder Reactions: Methods, Mechanistic Fundamentals, Pathways, and Applications," Angew. Chem. Int. Ed., (2002), 41:1650-1667.
European extended search report for EP Appl. No. 12763567.0 dated Oct. 20, 2014.
European Office Action dated Apr. 17, 2015 in European Patent Application No. 11743404.
Extended European Search Report issued on 12754746,5, mailed Apr. 23, 2015.
Futatsugi, et al., "Oxazaborolidine-Derived Lewis Acid Assited Lewis Acid as a Moisture-Tolerant Catalyst for Enantioselective Diels-Alder Reactions," Angew. Chem. Int. Ed., (2005), 44:1484-1487.
International Preliminary Report on Patentability for PCT/US2012/071052, issued Jun. 23, 2015.
Jana et al., "Progress in the Synthesis of Iboga-alkaloids and their Congeners," Organic Preparation and Procedures International, (2011), 43:541-573.
Jana et al., "Total synthesis of ibogaine, epiibogaine and their analogues", Tetrahedron. 2012. vol. 68, pp. 7155-7165.
Jarraya, et al., "N-(Hydroxymethyl)ibogaine," Acta Cryst., (2008), E64—vol. 64(9):o1739.
Kagan, et al., "Catalytic Asymmetric Diels-Alder Reactions," Chem. Rev., (1992), 92:1007-1019.
Kingston et al., "Cytotoxicity of Modified Indole Alkaloids", Journal of Pharmaceutical Sciences, 68:11, Nov. 1979, pp. 1403-1405.

Kontrimaviciute et al., "Liquid chromatography-electrospray mass spectrometry determination of ibogaine and noribogaine in human plasma and whole blood: Application to a poisoning involving Tabernanthe iboga root" J. Chromatog. B (2006), 843, 131-41.
Kuehne et al., "Biomimetric syntheses of indole alkaloids. 11. Syntheses of .beta.-carboline and indoloazepine intermediates," J. Org. Chem., (1985), 50(7):919-924.
Kuroch et al., "Voacanga Africana: Chemistry, Quality and Pharmacological Activity" ACS Symposium Series 1021 (African Natural Plant Products), (2009), 363-80.
Leonard, J. "A Practical Introduction to Separation and Purification techniques for the Beginning Organic Chemistry Laboratory", Chem. Ed. (1981), 58, 1022-23.
Lewis, "Studies on the synthesis and biosynthesis of indole alkaloids", The Faculty of Graduate Studies Department of Chemistry University of British Columbia, (1978), See compound 220, Figure 57. abstract only.
Naikwadi et al., "Liquid Chromatography of Phenolic Compounds on a Microbore Anion Exchange Resin Column," Analytical Chemistry, 56:8, 1984, p. 1525-1527.
Office Action on Japanese Application 2013-520892, mailed Jul. 7, 2015.
PCT International Preliminary Report on Patentability for PCT/US2012/067629 dated Nov. 13, 2014.
PCT International Search Report and Written Opinion dated Dec. 8, 2014 for PCT Application No. PCT/US2014/031364.
PCT International Search Report and Written Opinion dated Jan. 21, 2015 in PCT Patent Application No. PCT/US2014/034826.
PCT International Search Report and Written Opinion for related PCT/US2013/022874, dated Jun. 28, 2013.
Sjostromt et al., "Ion Exchange Separation Method for Microdetermination of Tropane Alkaloids in the Presence of Mkphine," 1959, XP55182014.
Stevenson et al, (Ed.), "Chiral Separations", Plenum Press (1987).
Still, et al., "Rapid Chromatorgraphic Technique for Preparative Separations with Moderate Resolutions", J. Org. Chem., (1978), 43, 2923-25.
Third Office Action on Chinese Application 201180038173.7, issued Jun. 17, 2015—English translation provided.
Toda, Fumio (Ed.), "Enantiomer Separation: Fundamentals and Practical Methods", Kluwer Academic Publishers (2004).
Toyo'oka, "Resolution of chiral drugs by liquid chromatography based upon diastereomer formation with chiral derivatization reagents", J. Biochem. Biophys. Methods 54, 25-56 (2002).
Trost, et al., "A Total Synthesis of Racemic and Optically Active Ibogamine. Utilization and Mechanism of a New Silver Ion Assisted Palladium Catalyzed Cyclization," J. Am. Chem. Soc., (1978), 100(12):3930-3931.
Trost, et al., "Stereocontrolled Approach to 1,4-Disubstitued 1,3-Dienes," J. Org. Chem., (1978), 43(24):4559-4564.
Office Action on Chinese Application 201110083808.7, mailed Jul. 15, 2015 English translation.
Office Action on Chinese Application 201280058362.5, issued Aug. 5, 2015, English translation provided.
Communication issued on EP 11743404.3, mailed Nov. 16, 2015.
Office Action issued on Chinese Application 201180038173.7, mailed Jan. 8, 2016, English translation provided.
Office Action issued on Russian Application 2013139382, mailed Dec. 4, 2015, English translation provided.
Office Action on Chinese Application 201110083808.7, mailed Jul. 15, 2015 English translation provided.
Russian Office Action on Application 2013102923/15 dated May 8, 2015, English translation included.
Vutukuri et al., "A Mild Deprotection Strategy for Allyl-Protecting Groups and Its Implications in Sequence Specific Dendrimer Synthesis," J.Org. Chem, vol. 68, 2003, pp. 1146-1149.
Examination Report issued on Australian Application 2012209332, mailed Feb. 10, 2016.
Second Office Action issued on Chinese Application 201280058362.5, mailed Feb. 22, 2016 English translation included.

\* cited by examiner

METHODS AND COMPOSITIONS FOR PREPARING AND PURIFYING NORIBOGAINE

CROSS-REFERENCE TO RELATED APPLICATIONS

This application is a continuation-in-part application of allowed U.S. patent application Ser. No. 13/104,406, filed May 10, 2011 now U.S. Pat. No. 8,765,737, which claims priority under 35 U.S.C. §119(e) to U.S. Provisional Patent Application Ser. No. 61/333,476, filed on May 11, 2010, and to U.S. Provisional Patent Application Ser. No. 61/419,772, filed on Dec. 3, 2010, all of which applications are incorporated by reference herein in their entirety.

FIELD OF THE INVENTION

This invention relates generally to methods and compositions for purifying the non-addictive alkaloid noribogaine.

BACKGROUND OF THE INVENTION

Noribogaine is a well known derivative of ibogaine and is sometimes referred to as 12-hydroxyibogaine. It is a metabolite of ibogaine. U.S. Pat. No. 2,813,873 claims noribogaine albeit as "12-O-demethylibogaine" while providing an incorrect structural formula for ibogaine. The structure of noribogaine has now been thoroughly evaluated and is found to combine the features of tyrptamine, tetrahydrohavaine and indolazepines. Noribogaine can be depicted by the following formula:

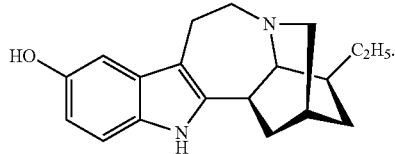

Noribogaine and its pharmaceutically acceptable salts have recently received significant attention as a non-addictive alkaloid useful in treating drug dependency (U.S. Pat. No. 6,348,456) and as a potent analgesic (U.S. Pat. No. 7,220,737).

Conventionally, noribogaine is prepared by demethylation of naturally occurring ibogaine:

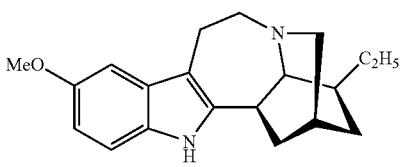

which is isolated from *Tabernanth iboga*, a shrub of West Africa. Demethylation may be accomplished by conventional techniques such as by reaction with boron tribromide/methylene chloride at room temperature followed by conventional purification.

Ibogaine possesses hallucinogenic properties. It is a Schedule 1-controlled substance as provided by the US Food and Drug Administration. Accordingly, methods for preparing noribogaine from ibogaine require high levels of assurance that contamination with unacceptable levels of ibogaine is avoided. As above, a one-step method for preparation of noribogaine from ibogaine via demethylation does not provide the requisite assurance that ibogaine will consistently be removed as a potential contaminant.

Accordingly, there is an ongoing need to provide a method for preparing noribogaine from ibogaine wherein any ibogaine contamination of noribogaine can be effectively and repeatedly minimized.

SUMMARY OF THE INVENTION

This invention provides methods and compositions for the preparation of noribogaine wherein contamination by ibogaine is predictably reduced to acceptable levels. In particular, this invention employs the use of solid supports to effect separation of noribogaine from ibogaine such that any ibogaine contamination is significantly reduced if not essentially eliminated.

Accordingly, in one of its method aspects, this invention is directed to a method for preparing and purifying noribogaine which method comprises:

a) converting ibogaine to noribogaine wherein the indole nitrogen is optionally protected by an amino protecting group;

b) attaching noribogaine to a solid support via the hydroxyl group of noribogaine, or via the hydroxylate anion of noribogaine, so as to form a suspension of solid supports having noribogaine bound thereto;

c) removing residual ibogaine from said suspension;

d) cleaving and recovering noribogaine from the solid support; and e) optionally repeating steps b), c) and d) up to 5 times;

f) purifying noribogaine as recovered per above.

In another of its method aspects, this invention is directed to a method for preparing and purifying noribogaine which method comprises:

a) covalently attaching ibogaine to a solid support via the amino group of ibogaine so as to form a suspension of solid supports having ibogaine bound thereto;

b) converting ibogaine to noribogaine under conditions wherein the level of ibogaine bound to the solid support is less than about 0.1 weight percent;

c) cleaving and recovering noribogaine from the solid support; and d) purifying noribogaine as recovered per above.

In yet another of its method aspects, this invention is directed to a method for separating and purifying noribogaine, which method comprises:

a. providing a solution comprising ibogaine and noribogaine;

b. contacting the solution with a solid support, wherein the solid support binds noribogaine but does not bind ibogaine, whereby a suspension comprising solid supports having noribogaine bound thereto is formed;

c. removing ibogaine from the suspension;

d. recovering noribogaine from the suspension; and e. purifying noribogaine.

In this aspect of the invention, steps (b), (c), (d) and (e) are optionally repeated. The purified noribogaine from step (f) comprises residual ibogaine at less than about 50 ppm, or less than about 10 ppm.

Further to this aspect of the invention, the step of purifying noribogaine comprises:

a. contacting the recovered noribogaine from step (e) with a solid support in an aqueous solution, wherein the solid support ionically binds to noribogaine, and wherein ibogaine does not ionically bind to the solid support, whereby a suspension comprising solid supports having noribogaine ionically bound thereto is formed;
b. removing ibogaine from the suspension;
c. eluting noribogaine from the solid supports in the suspension; and
d. recovering noribogaine from the suspension.

Further to this aspect of the invention, the solid support is an anion exchange resin. Preferably, the aqueous solution is at a pH of about 10 or more, such that noribogaine can also be present as the phenoxide of noribogaine.

In one of its composition aspects, this invention is directed to a solid support having ibogaine or noribogaine covalently bound thereto through a cleavable linker.

In one embodiment, the solid support of this invention comprises ibogaine covalently bound thereto through a cleavable linker. In another embodiment, the solid support of this invention comprises noribogaine covalently bound thereto through a cleavable linker.

In another one of its composition aspects, this invention is directed to an ion exchange resin having noribogaine ionically bound thereto through the anion of noribogaine's phenoxide functional group.

In yet another one of its composition aspects, this invention is directed to a composition comprising an ion exchange resin having noribogaine ionically bound thereto through the anion of noribogaine's phenoxide functional group in an aqueous solution of pH 10 or more.

Also provided by this invention are purification columns comprising an ion exchange resin having, for example, noribogaine ionically bound thereto through the anion of noribogaine's phenoxide functional group, or having noribogaine ionically bound thereto through the anion of noribogaine's 12-hydroxy functional group.

DETAILED DESCRIPTION OF THE INVENTION

This invention is directed to methods and compositions comprising noribogaine and, in particular, methods and compositions comprising highly pure noribogaine. However, prior to describing this invention in greater detail, the following terms will first be defined.

It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

It must be noted that as used herein and in the appended claims, the singular forms "a", "an", and "the" include plural referents unless the context clearly dictates otherwise. Thus, for example, reference to "a pharmaceutically acceptable excipient" includes a plurality of such excipients.

1. Definitions

Unless defined otherwise, all technical and scientific terms used herein have the same meaning as commonly understood by one of ordinary skill in the art to which this invention belongs. As used herein the following terms have the following meanings As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

The term "about" when used before a numerical designation, e.g., temperature, time, amount, and concentration, including range, indicates approximations which may vary by (+) or (−) 10%, 5% or 1%.

As stated above, the invention is directed to compositions comprising noribogaine and an excipient to facilitate transport across the blood brain barrier.

As used herein, the term "noribogaine" refers to the compound:

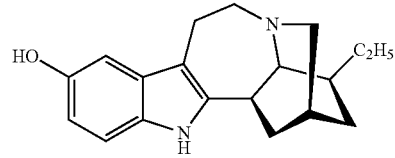

and salts thereof. Conventionally, noribogaine is prepared by demethylation of naturally occurring ibogaine:

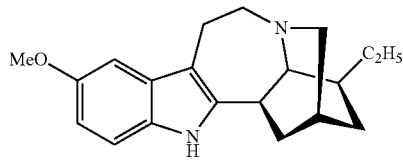

which is isolated from *Tabernanth iboga*, a shrub of West Africa. Demethylation may be accomplished by conventional techniques such as by reaction with boron tribromide/methylene chloride at room temperature, or reaction with lithium diphenylphosphine (preferably an excess thereof), followed by conventional purification. This invention is not limited to any particular chemical form of noribogaine and the compound may be present as either as a free base or as an acceptable addition salt.

The term "solid support" refers to a material having a rigid or semi-rigid surface which contain or can be derivatized to contain reactive functionality which covalently links noribogaine or ibogaine to the surface thereof through a cleavable linker. Such materials are well known in the art and include, by way of example, silica, synthetic silicates, biogenic silicates, porous glass, hydrogels, silicate-containing minerals, synthetic polymers, polystyrene, polypropylene, polyacrylamide, polyethylene glycol, polyacrylamide and copolymers thereof including copolymers of polystyrene/polyethylene glycol and polyacrylamide/polyethylene glycol, and the like.

As used herein, the term "ion exchange resin" refers to an insoluble organic polymer containing charged groups that attract and hold oppositely charged ions present in a surrounding solution in exchange for counterions previously held. Suitable ion exchange resins to be used herein contain cationic groups that attract and hold anions present in a surrounding solution, and are sometimes referred to as "anion exchange resins".

As used herein, the term "cleavable linking arms" refers to linking arms, which are a chemical group or a covalent bond which covalently attaches at one end to a solid support and at the other end to ibogaine or noribogaine. At least one of the covalent bonds of the linking arm which attaches ibogaine or noribogaine to the solid support can be readily broken by specific chemical or enzymatic reactions, thereby providing for ibogaine or noribogaine free of the solid support. The chemical or enzymatic reactions employed to break the covalent bond of the linking arm are selected so as to be specific for bond breakage thereby preventing unintended reactions occurring elsewhere on the compound. The cleavable linking group is selected relative to ibogaine/noribogaine formed on the solid support so as to prevent premature cleavage of either ibogaine or noribogaine from the solid support as well as not to interfere with any of the procedures employed during synthesis on the support. Suitable cleavable linking arms are well known in the art, and may include such groups as carbonate groups, carbamate groups, amide groups, and the like. In a preferred embodiment, the cleavable linker arm contains no more than 10 atoms. More preferably, the cleavable linker contains from 1 to 4 carbon atoms and from 2 to 4 heteroatoms selected from oxygen, nitrogen, sulfur, $S(O)$ and $S(O)_2$.

As used herein, the term "an acceptable addition salt" refers to pharmaceutically acceptable salts of a compound of Formula I which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

As used herein, the term "protecting group" or "Pg" refers to well known functional groups which, when bound to a functional group, render the resulting protected functional group inert to the reaction conditions to be conducted on other portions of the compound and which, at the appropriate time, can be reacted to regenerate the original functionality. The identity of the protecting group is not critical and is selected to be compatible with the remainder of the molecule. In one embodiment, the protecting group is an "amino protecting group" which protects the amino functionality of ibogaine or noribogaine during the reactions described herein. Examples of conventional amino protecting groups include, for instance, benzyl, acetyl, oxyacetyl, carboxybenzyl (Cbz), and the like. In another embodiment, the protecting group is a "hydroxy protecting group" which protects the hydroxyl functionality of noribogaine. Examples of hydroxyl protecting groups include, for instance, benzyl, p-methoxybenzyl, p-nitrobenzyl, allyl, trityl, dialkylsilylethers, such as dimethylsilyl ether, and trialkylsilyl ethers such as trimethylsilyl ether, triethylsilyl ether, and t-butyldimethylsilyl ether; esters such as benzoyl, acetyl, phenylacetyl, formyl, mono-, di-, and trihaloacetyl such as chloroacetyl, dichloroacetyl, trichloroacetyl, trifluoroacetyl; and carbonates such as methyl, ethyl, 2,2,2-trichloroethyl, allyl, benzyl, and p-nitrophenyl. Additional examples of hydroxy protecting groups may be found in standard reference works such as Greene and Wuts, Protective Groups in Organic Synthesis., 2d Ed., 1991, John Wiley & Sons, and McOmie Protective Groups in Organic Chemistry, 1975, Plenum Press.

Preparation and Purification of Noribogaine

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, Protecting Groups in Organic Synthesis, Fourth Edition, Wiley, N.Y., 2007, and references cited therein.

Furthermore, the compounds of this invention will typically contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

It is contemplated that noribogaine can be prepared and/or purified from ibogaine by utilizing solid support as shown in the following Schemes, where PG represents an amine protecting group, LG represents a leaving group (e.g. a halo or alcohol), L represents a cleavable linking group (e.g. a carbonyl compound such as a carbonate or carbamate) and the shaded circle represents a solid support. In the following Schemes, the O-demethylation of the aryl methoxy group to provide the corresponding phenol can be accomplishing using any suitable method known in the art. Suitable reagents include a Lewis acid (e.g. $BBr_3$, $AlCl_3$), a nucleophile (e.g. RS—, $N_3$—, SCN—), NaCN at low pH (e.g. pH 12), lithium diphenylphosphine (preferably an excess thereof), and the like. In some embodiments, the O-demethylation should be performed without affecting the linkage to the solid support. Suitable reagents can be readily ascertained by one of skill in the art and can be found, for example, in T. W. Greene and G. M. Wuts, Protecting Groups in Organic Synthesis, Fourth Edition, Wiley, N.Y., 2007 (see, e.g., the reactivity charts at pages 1006-1008 and 1022-1032), and references cited therein.

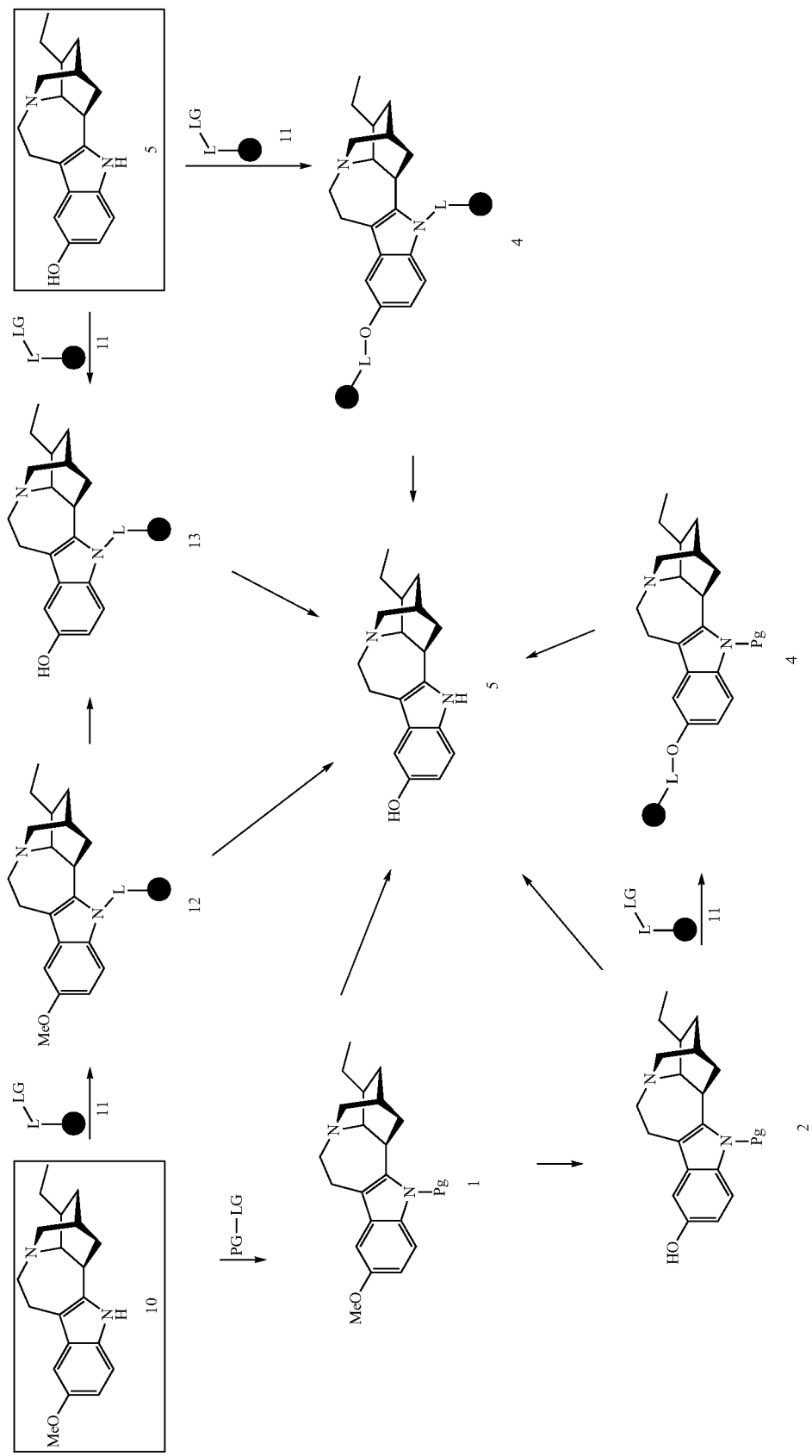

Noribogaine 5 can be prepared and purified from ibogaine 10 by any one of the routes shown in Scheme 1. Noribogaine, compound 5, is differentiated from ibogaine by virtue of the fact that the methoxy group of ibogaine has been converted to a hydroxyl group in noribogaine. In one embodiment, the indole amine of ibogaine can be protected using an amine protecting group to provide compound 1, followed by either tandem O-demethylation and removal of the protecting group using L-selectride®, for example, or sequential O-demethylation and removal of the protecting group to provide noribogaine 5. In addition, in one embodiment, noribogaine can be directly prepared and purified from the O-demethylation of ibogaine using methods known in the art and then purified by appending noribogaine to a solid support (compound 12 or 13), washing any contaminants, cleaving the linking group L, and recovering the noribogaine 5. In the above syntheses, one or more of the noribogaine or intermediates shown above can be purified using standard purification techniques known in the art (e.g. column chromatography, HPLC, and the like). Compounds of formula 11 are commercially available or can be synthesized in one or two steps from commercially available starting materials (see, e.g. commercially available resins from Sigma-Aldrich®).

In one preferred embodiment, purification techniques can be used to maximize the purity of the recovered noribogaine. In one embodiment, noribogaine can be contacted with a suitable ion exchange resin at a pH where the phenol group has deprotonated to a sufficient degree such that these compounds are suitable for purification. Typically for phenol deprotonation, a pH of 10 or greater is used. As ibogaine does not have an ionizable phenolic group, it will not bind to the ion exchange resin and can thus be eluted from column and separated from the resin-bound noribogaine. Suitable ion exchange resins are commercially available and include, but are not intended to be limited to Amberlite® anion exchange resin, Toyopearl® anion exchange resin, Lewatit® anion exchange resin, Dowex® anion exchange resin, Diaion™ anion exchange resin, and Amberlyst® anion exchange resin (Sigma Aldrich, Inc.).

In yet another of its method aspects, this invention is directed to a method for separating and purifying noribogaine by providing a solution comprising ibogaine and noribogaine and then contacting the solution with a solid support which binds to noribogaine but does not bind ibogaine, whereby a suspension comprising solid supports having noribogaine bound thereto is formed. Ibogaine is then removed from the suspension-and then noribogaine is recovered and purified. It is to be understood that, prior to the purification step, the steps preceding purification can be optionally repeated such that the purified noribogaine comprises residual ibogaine at less than about 50 ppm, or less than about 10 ppm.

According to this aspect of the invention, noribogaine is purified by contacting the recovered noribogaine with a solid support in an aqueous solution, preferably at a pH of about 10 or more, such that noribogaine is or can be present in the form of the phenoxide of noribogaine, wherein the solid support ionically binds to noribogaine but ibogaine does not ionically bind to the solid support, such that a suspension comprising solid supports having noribogaine ionically bound thereto is formed. Ibogaine is then removed from the suspension, noribogaine eluted from the solid supports, and then noribogaine is recovered.

In this aspect of the invention, the solid support is an anion exchange resin. The anion exchange resin can be selected from commercially available anion exchange resins known in the art, including but not limited to Amberlite IRA-120® anion exchange resin, Purolite A-510® anion exchange resin, Dowex XZ® anion exchange resin and Dowex 1-X8® anion exchange resin (Sigma Aldrich, Inc.).

In one of its composition aspects, this invention is directed to an ion exchange resin having noribogaine ionically bound thereto through the anion of noribogaine's phenoxide functional group.

In another one of its composition aspects, this invention is directed to a composition comprising an ion exchange resin having noribogaine ionically bound thereto through the anion of noribogaine's phenoxide functional group in an aqueous solution of pH 10 or more.

Also provided by this invention are purification columns comprising an ion exchange resin having, for example, noribogaine ionically bound thereto through the anion of noribogaine's phenoxide functional group, or having noribogaine ionically bound thereto through the anion of noribogaine's 12-hydroxy functional group.

Accordingly, in one of its composition aspects, there is provided an aqueous solution having a pH of at least 10 and a compound of the formula:

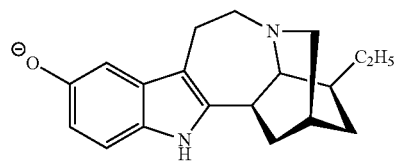

The purification process typically comprises pretreating or washing the resin with a solvent system which has the same pH, and other components such buffers, stabilizers, etc., that will be used to dissolve the noribogaine or salt thereof ("wash solvent"). Washing preferably includes passing at least 1 void volume (the volume of solvent needed to fill the resin vessel) of the wash solvent through the resin under ambient conditions. Subsequently, noribogaine is added to the same solvent system used as the wash solvent at a concentration preferably less than the saturation concentration for noribogaine. Noribogaine may be present as the phenolic anion under these conditions and, accordingly, both will bind to the anion exchange resin while other compounds lacking an anionic charge (i.e. ibogaine) will pass through the resin. Elution of the purified noribogaine can be then be accomplished using a cation-containing solution.

Accordingly, in another of its composition aspects, there is provided an anion exchange resin comprising an aqueous solvent system and a pH of at least 10 and either compound 2a or compound 4a bound thereto.

In one embodiment, noribogaine can be prepared and purified from ibogaine in the manner described in Scheme 2 below:

SCHEME 2

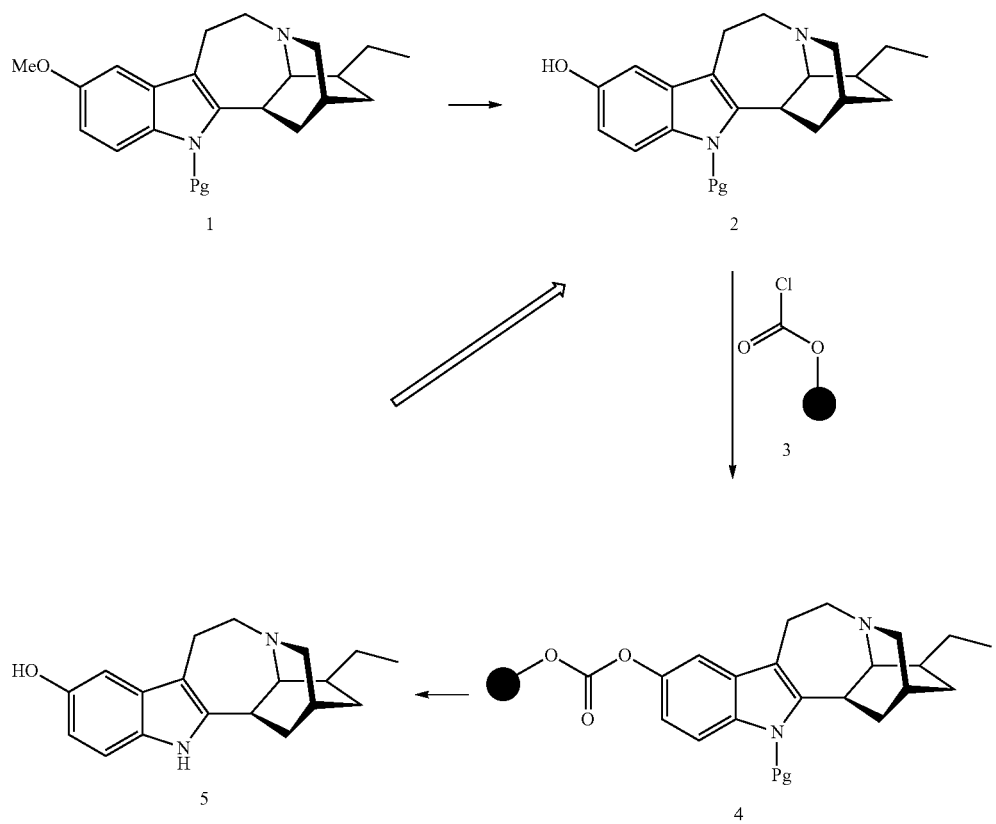

wherein Pg is hydrogen or an amino protecting group and the shaded circle represents a solid support.

Specifically, in Scheme 2, amino protected ibogaine, compound 1, is contacted with boron tribromide in methylene chloride or lithium diphenylphosphine using conditions well known in the art to provide for the amino protected noribogaine, compound 2.

In Scheme 2, attachment of amino protected noribogaine, compound 2, to a solid support is accomplished by use of a chloroformate/solid support, compound 3, under conventional conditions to provide for compound 4 wherein the carbonate group is shown for illustrative purposes only as the cleavable linking group. Other cleavable linkers can likewise be used in Scheme 2. As amino protected ibogaine does not contain a functional group reactive with compound 3, only amino protected noribogaine, compound 2, will react with the solid support and provide for compound 4. Repeated washing of compound 4 will remove amino protected ibogaine contaminating the sample of amino protected noribogaine used in this reaction. Furthermore, at any time, a small portion of the solid support can be removed to provide a sample of noribogaine (after cleavage and deprotection). The sample can then be analyzed for purity relative to any ibogaine present by conventional methods such as GC/MS, NMR, $C^{13}$-NMR, etc.

Upon achieving the desired level of purity of noribogaine relative to any contaminating ibogaine, noribogaine, compound 5, can be recovered from the solid support by cleavage of the cleavable linker and subsequent deprotection of the amino group. Both cleavage and deprotection are well known in the art.

As desired, exceptionally pure noribogaine, compound 5, can be obtained by repeating the process of forming the amino protected noribogaine, compound 2, binding compound 2 to a solid support via the hydroxyl group of amino protected noribogaine and washing any contaminating ibogaine from the solid support. By repeating this process as often as necessary and preferably no more than 5 times, it is contemplated that noribogaine having less than 5 ppm ibogaine and preferably less than 100 ppm ibogaine can be prepared.

In another embodiment, noribogaine can be prepared and purified from ibogaine in the manner described in Scheme 3 below:

SCHEME 3

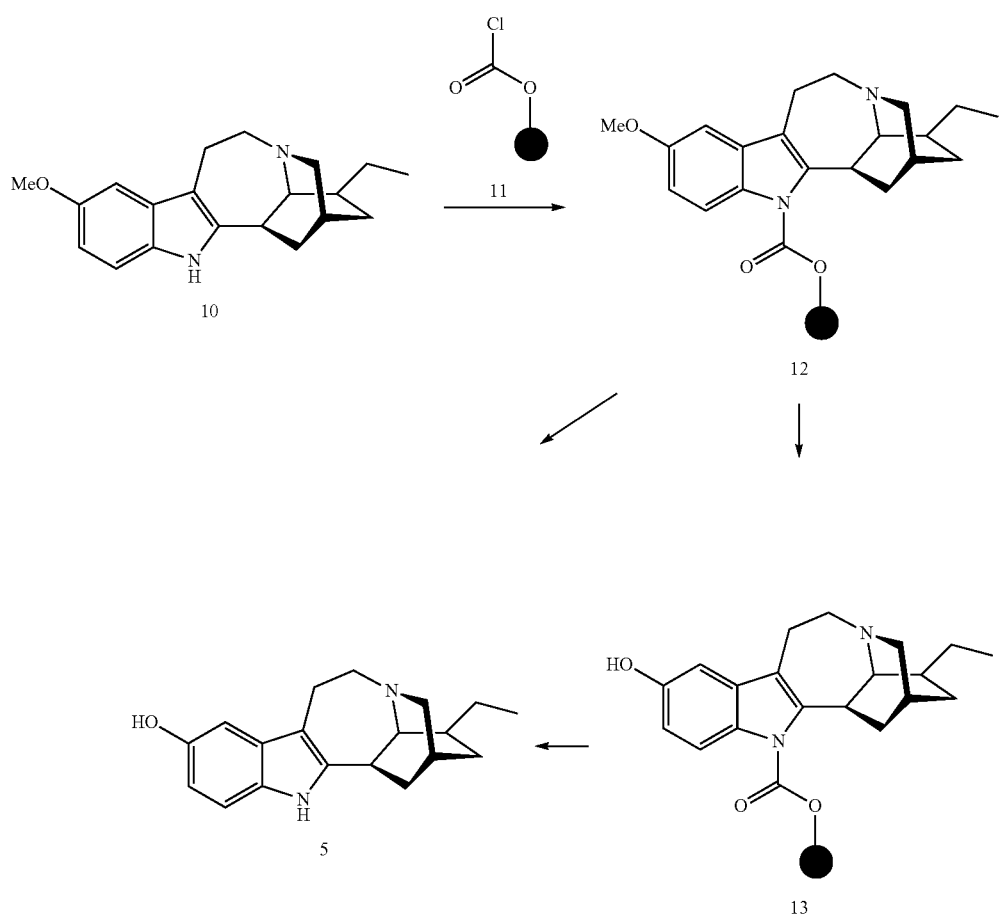

In Scheme 3, ibogaine, compound 10, is bound via conventional techniques to a solid support, compound 11, through a cleavable linker arm which, for the sake of illustration only, is depicted as a carbamate bond in resulting compound 12. Compound 12 is then contacted with boron tribromide in methylene chloride or lithium diphenylphosphine using conditions well known in the art to provide for the noribogaine bound via the indole nitrogen to a solid support, compound 13. Cleavage of the cleavable linker in compound 13 provides for noribogaine, compound 5. In certain embodiments, compound 5 can be directly obtained from compound 12 using a reducing agent (e.g. L-Selectride®). See U.S. Pat. No. 6,291,675.

In one embodiment, compound 5 can be purified by conventional techniques including high performance liquid chromatography (HPLC) and the purity level of the resulting purified compound confirmed by GC/MS. Alternatively, compound 5 can be used in Scheme 2 as recited above by attaching a solid support to the hydroxyl functionality. In either case, very high levels of noribogaine purity can be obtained.

The following synthetic and biological examples are offered to illustrate this invention and are not to be construed in any way as limiting the scope of this invention. Unless otherwise stated, all temperatures are in degrees Celsius.

EXAMPLES

In the examples below, the following abbreviations have the following meanings. If an abbreviation is not defined, it has its generally accepted meaning Example 1

Synthesis and Purification of Noribogaine from Ibogaine

Example 1 illustrates one method for the synthesis and purification of noribogaine from ibogaine which method follows Scheme 4 below:

SCHEME 4

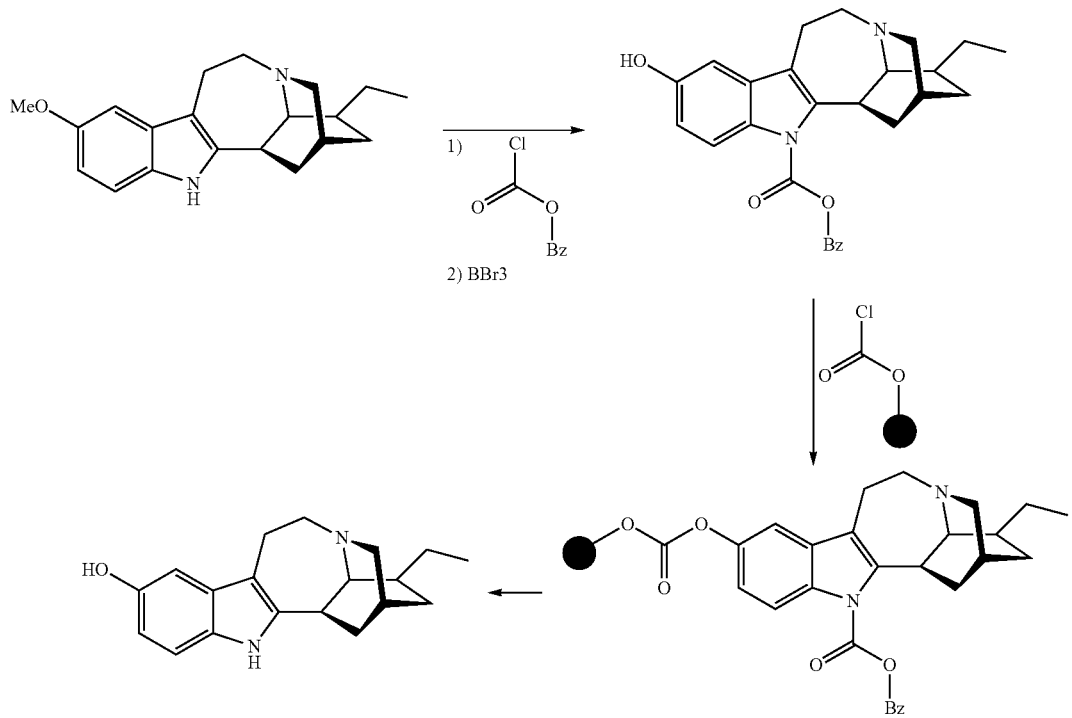

Specifically, in Scheme 4, ibogaine is contacted with a stoichiometric excess of benzyl chloroformate in an inert solvent such as methylene chloride. The reaction mixture further contains at least a stoichiometric equivalent of diisopropylethylamine relative to ibogaine so as to scavenge the acid generated during the reaction. The reaction is maintained at room temperature under an inert atmosphere until the reaction is substantially complete as evidenced by, for example, thin layer chromatograpy. At which time, an O-demethylation reagent (e.g. boron tribromide, aluminum trichloride, or lithium diphenylphosphine), or preferably a stoichiometric excess thereof, is added to the reaction mixture which is then maintained under conditions (e.g. room temperature) wherein the methoxy group of ibogaine has been converted to the hydroxyl group of noribogaine.

The hydroxyl group generated above is then employed as a complementary functionality for attachment of a solid support. In particular, an excess of chloroformate bound to a solid support is combined with N—CBZ-noribogaine under conventional conditions wherein a cleavable carbonate bond is formed. Chloroformate bound to a solid support can be prepared from a hydroxy-bearing polymer support (e.g. hydroxymethyl) polystyrene or polymer-bound benzyl alcohol, both commercially available from Sigma-Aldrich®) and carbonyl dichloride. As CBZ-ibogaine does not readily react under these O-demethylation conditions, it will remain in the solution phase of the reaction mixture and can be washed from the reaction mixture by conventional techniques including placing the solid support into a column and passing excess solvent through the column.

In one particular example, 1 kg of solid support containing CBZ-noribogaine is loaded onto a column. The stopper of the column is partially opened so that a flow rate through the column of 0.5 liters per hour is maintained. Methylene chloride is continuously fed to the top of the column and recovered at the base of the column. The recovered methylene chloride is stripped to provide residual CBZ-ibogaine. The process is continued until the effluent from the column no longer contains CBZ-ibogaine. At which time, a portion of the solid support is loaded into a hydrogenation vessel together with methanol and a catalytic amount of palladium on carbon. Hydrogenation is continued under elevated pressure for approximately 5 hours. The reaction is then stopped and the methanol recovered and stripped to provide for noribogaine. Additional purification of noribogaine can be achieved by HPLC as desired.

What is claimed is:

1. An ion exchange resin having noribogaine ionically bound thereto through the anion of noribogaine's phenoxide functional group, wherein the resin is essentially free of ibogaine or the resin comprises ibogaine.

2. The ion exchange of claim 1, wherein the resin is essentially free of ibogaine.

3. The ion exchange of claim 1, wherein the resin comprises ibogaine.

4. A composition comprising the ion exchange resin of claim 1 and an aqueous solution of pH 10 or more.

5. A purification column comprising the ion exchange resin of claim 1.

* * * * *